United States Patent [19]

Gupta

[11] Patent Number: 5,164,311
[45] Date of Patent: Nov. 17, 1992

[54] PREPARATION OF AN ANTIBODY-ENZYME CONJUGATE

[75] Inventor: Ravinder K. Gupta, Pembroke Pines, Fla.

[73] Assignee: Coulter Corporation, Hialeah, Fla.

[21] Appl. No.: 855,444

[22] Filed: Mar. 19, 1992

Related U.S. Application Data

[63] Continuation of Ser. No. 482,215, Feb. 20, 1990, abandoned.

[51] Int. Cl.⁵ ................... C12N 9/96; G01N 33/535
[52] U.S. Cl. ........................ 435/188; 435/7.9; 435/174; 435/964; 435/972; 436/512; 436/547; 436/548; 530/402; 530/391.5
[58] Field of Search ........... 435/7.1, 7.9, 174, 188, 435/964, 972; 436/512, 519, 541, 547, 548; 530/390, 402, 404, 806

[56] References Cited

U.S. PATENT DOCUMENTS 4,228,237 10/1980 Herey et al. ............... 435/188 X
4,684,609 8/1987 Hsu .......................... 435/188 X
4,894,229 1/1990 Polson et al. ............... 435/181 X
5,002,883 3/1991 Bieniarz et al. ............. 435/176

OTHER PUBLICATIONS

Imagawa et al., Journal of Applied Biochemistry, 4 (1982), pp. 41-57.

*Primary Examiner*—David M. Naff
*Attorney, Agent, or Firm*—Myron C. Cass

[57] ABSTRACT

An antibody-enzyme conjugate is prepared having an enzyme to antibody ratio of approximately 3. The conjugate is produced by adding sulfhydryl groups to an antibody and maleimidyl groups to an enzyme to produce a modified antibody and enzyme, and reacting the modified antibody and enzyme to produce the conjugate. In producing the modified antibody and enzyme, about a 15 molar excess of reagents for introducing sulfhydryl and maleimidyl groups is used. When reacting the modified antibody and enzyme, a four molar excess of the modified enzyme is used, and reacting is stopped after a specified period of time by addition of selective reagents. The selective reagents may be cysteine and iodoacetamide.

6 Claims, No Drawings

PREPARATION OF AN ANTIBODY-ENZYME CONJUGATE

This is a continuation of application Ser. No. 07/482,215 filed Feb. 20, 1990, now abandoned.

FIELD OF THE INVENTION

This invention relates generally to enzyme immunoassays and immunochemistry involving antibody-enzyme conjugates, and more particularly, relates to an improved antibody-enzyme direct conjugate for use in such assays which provides an enhanced enzyme-to-antibody ratio for a desirable high degree of sensitivity, and to the method for making the conjugate.

BACKGROUND OF THE INVENTION

Methods for detecting the presence and/or quantity of an immunoreactant, such as an antibody or antigen, present in a human physiological fluid or tissue test sample often employ labelled reagents in a specific complexing process for the detection of these immunoreactants. Commonly used labels include radioactive, enzymatic, fluorescent and chemiluminescent labels. The label chosen for a particular detection method often depends upon the balancing of the advantages and disadvantages of the labels under consideration. Factors such as label size, label stability, available instrumentation, practicability and sensitivity influence the choice of label. See R. M. Dauphinais, Solving and preventing problems in ligand assay, in N. R. Rose et al., Manual of Clinical Laboratory Immunology, Third Edition, Ch. 16, pp. 88-98 (1986).

The avidin-biotin labelling technique has been shown to provide a high level of sensitivity. E. A. Bayer et al., The use of avidin-biotin complex as a tool in molecular biology. Methods Biochem. Anal. 26:1-43 (1980). Avidin is a basic glycoprotein derived from egg albumin which has a molecular weight of 68,000 daltons. It has a high affinity for the vitamin biotin which has a molecular weight of approximately 244 daltons. Each avidin molecule has four binding sites for biotin. The avidin-biotin system employs an immunoreactant which is usually an antibody linked to biotin and a label which is usually an enzyme linked to avidin. The strong interaction between avidin and biotin is used to link the biotinylated antibody to the enzyme-labelled avidin, thus serving as a means of amplifying the sensitivity of the immunoassay in which it is so used. The avidin-biotin labelling system thus has been employed to enhance sensitivity over other labelling systems, including the direct enzyme conjugate labelling system. U.S. Pat. No. 4,228,237 describes a method to determine the presence of a ligand, such as, a labelled antibody, in a liquid medium which utilizes enzyme-labelled avidin and a biotin labelled reagent. Also, U.S. Pat. No. 4,684,609 teaches a biotinavidin label and its use for labelling tissue sections.

Although the avidin-biotin labelling system can provide an enhanced signal over previous labelling systems, problems are encountered with its use. Since the biotin and avidin usually are coupled with a ligand and a label, an additional incubation step and additional washing steps are required to be performed. Furthermore, the hydrophobic nature of the biotin molecule gives rise to higher background "noise" and false positive reactions in the performance of an assay method which utilizes avidin and biotin. Background noise is herein defined as the binding of the labelled species or fragments thereof to reagents in the assay system which causes non-specific precipitation of interference that is unrelated to the specific protein-bound fraction.

Direct antibody-enzyme conjugates are well known in the immunoassay art and have been described in the literature. See, for example, E. Ishikawa et al., J. Immunochemistry 4(3):209-327 (1983). The degree of sensitivity obtained with these direct antibody-enzyme conjugates, however, often is much lower than the degree of sensitivity obtained with the avidin-biotin system. This lower degree of sensitivity is due to the low enzyme-to-antibody ratio obtained for these conjugates in these preparations. In fact, the majority of these direct antibody-enzyme conjugate preparations give enzyme-to-antibody rations of 0.3 to 1.0 (E. Ishikawa, ibid, page 221). Higher enzyme-to-antibody ratios usually are not desirable, if obtainable, because of the potential loss in antibody activity and higher background "noise".

It would be advantageous to provide a labelling system wherein direct antibody-enzyme conjugates could achieve high enzyme-to-antibody ratios and therefore provide a higher degree of sensitivity approaching or equal to the avidinbiotin labelling system. Such an improved direct antibody-enzyme conjugate would not require the additional incubation step and washing steps as the biotin-avidin labelling system requires. Also, such a system would avoid the problems of using a hydrophobic molecule such as biotin, and therefore, lessen the chance of higher background "noise" and false positive reactions.

The invention herein provides for such a improved direct antibody-enzyme conjugate and a labelling system for direct antibody-enzyme conjugates which achieves a high enzyme-to-antibody ratio of approximately three (3) without any significant loss of antibody activity or higher back ground "noise". This conjugate was prepared by using long chains between the antibody and enzyme molecules. In the procedure, sulfhydryl groups are introduced to the antibody. Additionally, maleimide groups are introduced into an enzyme, for example, Horseradish Peroxidase. This modified antibody and modified enzyme are combined and allowed to react. A mean enzyme-to-antibody ratio of approximately three (3) is achieved. A higher level of sensitivity is provided by the improved method without any increase in background "noise". Thus, one incubation and several washing steps required by the biotin-avidin labelling system are eliminated by the labelling system of this invention. It also eliminates the false positive reactions obtained by the use of hydrophobic biotin molecule in the biotin-avidin enzyme indirect method described hereinabove.

SUMMARY OF THE INVENTION

A direct antibody-enzyme conjugate is provided which achieves a high enzyme-to-antibody ratio of approximately three (3) and which, therefore, provides a higher degree of sensitivity than heretofore seen with direct antibody-enzyme conjugates.

The conjugate of the invention is prepared by a novel procedure wherein sulfhydryl groups are introduced to the antibody and maleimide groups are introduced to the enzyme. The thus-modified antibody and enzyme are combined in a suitable ratio to provide the direct antibody-enzyme conjugate.

PREFERRED EMBODIMENTS OF THE INVENTION

The method of the invention is practiced by performing a 3-step procedure. In STEP A, the antibody is modified by introducing sulfhydryl groups to the antibody. In STEP B, maleimide groups are introduced to the enzyme by using sulfosuccinimidyl 4-(N-maleimidomethyl) cyclohexane-1- carboxylate. In STEP C, direct conjugation is performed by suitably adapting a method described by S. Yoshitake et al., Eur. J. Biochem. 101:395–399 (1979).

A glossary of reagents employed in practicing the invention is as follows:

STEP A

Antibody, 20 mg/ml in 100 mM Phosphate,
150mM NaCl, 2mM EDTA, pH 7.4,
15 Molar excess of 2-iminothiolane hydrochloride
Sephadex ®G-50 Column.

STEP B

Horseradish Peroxidase (Sigma Chemical Co.),
DEAE Sepharose CL-6B column (Pharmacia),
2.5mM Potassium Phosphate, pH 8.0,
Sulfosuccinimidyl 4-(N-maleimidomethyl) cyclohexane-1carboxylete at 15 M excess.
100 mM Potassium Phosphate, 100 mM NaCl, pH 7.4

STEP C

Modified antibody from STEP A,
Modified peroxidase from STEP B,
Cysteine,
Iodoacetamide, pH 8.7,
Amicon YM-30 membrane (W. R. Grace & Co.),
TSK-250 FPLC column,

CONJUGATION PROCEDURE

Step A

A solution of a selected antibody (Ab) at 20 mg/ml in 100 mM phosphate, 150 mM NaCl, 2 mM EDTA, pH 7.4, is treated with a 15 molar excess of 2-iminothiolane hydrochloride (ITH) for one hour at 22° C. Then the reaction mixture is desalted over a Sephadex ® G-50 column. The product protein peak (I) is collected and its concentration is determined from the A280 value. The conjugating mechanism is represented diagrammatically as follows:

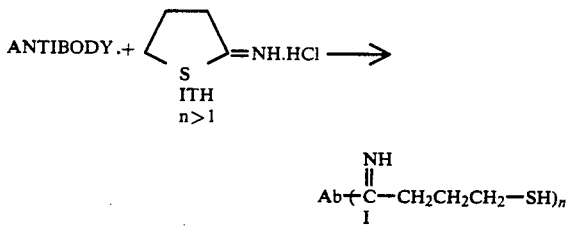

Step B

An enzyme (Ez) such as Horseradish Peroxidase (Sigma Chemical Co.) is purified over a DEAE Sepharose CL-6B column (Pharmacia) in 2.5mM Potassium Phosphate buffer, pH 8.0, and the pass through peak is collected. Purified horseradish peroxidase (at 13 mg/ml) is reacted with sulfosuccinimidyl 4-(N-maleimidomethyl) cyclohexane -1- carboxylate, SMCC, (Pierce Chemical Co.) at 15 molar excess in 100 mM Potassium Phosphate buffer, 100 mM NaCl pH 7.4 for one hour at between 21° and 25° C. The reaction mixture next is desalted over a Sephadex ®G-50 column and the product protein (II) peak is collected. The concentration of the protein peak is calculated for absorbence at 403nm. The reaction mechanism is represented diagrammatically as follows:

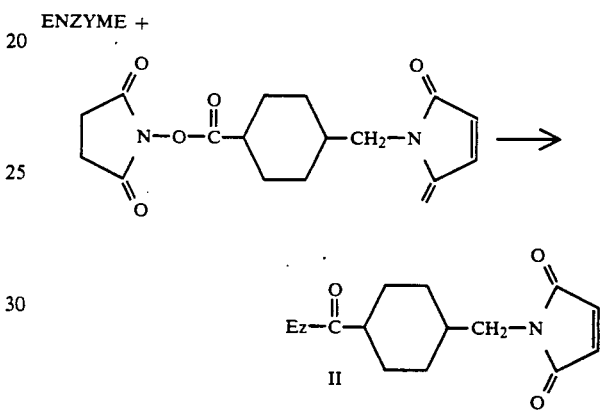

Step C

Modified antibody and modified peroxidase obtained by performing STEPS A and B as described herein next are combined with stirring to provide a four molar excess of peroxidase over antibody. This excess of modified peroxidase to modified antibody was chosen to produce a product having an enzyme-to-antibody ratio of approximately three (3). The reaction then is allowed to take place at 22° C. over two hours. (This conjugation procedure can be varied with respect to the time and temperature and still produce a conjugate with an enzyme-to-antibody ratio of approximately three (3).) The reaction is quenched by addition of cysteine to a 5mM concentration. After 15 minutes the reaction is further quenched by the addition of excess iodoacetamide at pH 8.7 for 30 minutes. The reaction mixture is concentrated over a YM-30 membrane and then it is chromatographed over a TSK-250 FPLC column. The protein peak is collected into various fractions and analyzed on a spectrophotometer. The conjugating mechanism is represented diagrammatically as follows:

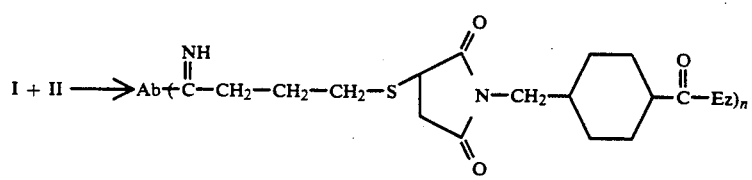

The enzyme used in this direct antibody-enzyme conjugate can vary. Examples of suitable enzymes for use in practicing the invention include horseradish peroxidase, alkaline phosphatase, galactose, oxidase and lactoperoxidase. Various antibodies can be employed which include polyclonal and monoclonal antibodies. Antibody fragments also can be employed. The human anti-HIV antibody was chosen for the example given below. In addition to 2-iminothiolane hydrochloride, other sulfhydral producing reagents useful in practicing this invention include N-succinimidyl 3-(2- pyridyl-dithio) propionate (SPDP) and N-succinimidyl-S-acetyl-thioacetate (SATA). Additional reagents capable of introducing maleimide groups include succinimidyl 4-(p-maleimidylphenyl) butyrate, m-maleimidobenzoyl-N-hydroxysulfosuccinimide ester, succinimidyl maleimidylacetate, and succinimidyl 6-maleimidylhexanoate.

A preferred embodiment is described by the following example:

EXAMPLE

A solution of human anti-HIV antibody was prepared as described in STEP A. Horseradish peroxidase was purified and reacted as described in STEP B. The modified human anti-HIV antibody and modified horseradish peroxidase were combined as described in STEP C. The first peak from the column gave the conjugate with a enzyme-antibody ratio value of 2.93.

The preferred embodiment can be varied by substituting the reagents specifically identified herein. The preferred ratio value of approximately 3 is to be noted.

We claim:

1. A method for producing an enzyme-antibody conjugate of molar ratio of about 3:1, said method comprising:
   (a) reacting an enzyme with about a 15 molar excess of a reagent capable of introducing maleimidyl groups into said enzyme, said reaction being carried out in a phosphate buffer solution of about pH 7.4 for a period of time of about 1 hour at a temperature of about 21°–25° C.;
   (b) reacting an antibody with about a 15 mole excess of a reagent capable of introducing sulfhydryl groups into said antibody, said reaction being carried out in a phosphate buffer solution of about pH 7.4 for a period of time of about 1 hour at a temperature of about 22° C.;
   (c) reacting the products of steps (a) and (b) in a selected proportion such that there is a four molar excess of (a) over (b), said reaction being carried out for a period of time of about 2 hours at a temperature of about 22° C.;
   (d) stopping the reaction of step (c) by the addition of selective reagents; and
   (e) concentrating the product of step (d) and purifying the same to thereby obtain said enzyme-antibody conjugate of said ratio molar about 3:1.

2. The method according to claim 1 wherein the antibody is a polyclonal antibody.

3. The method according to claim 1 wherein the antibody is a monoclonal antibody.

4. The method according to claim 1 wherein the antibody comprises an antibody fragment.

5. The method according to claim 1 wherein the enzyme is horseradish peroxidase.

6. The method of claim 1 wherein said stopping reagents are cysteine and iodoacetamide.

* * * * *